(12) United States Patent
Nevermann et al.

(10) Patent No.: US 7,005,451 B1
(45) Date of Patent: Feb. 28, 2006

(54) AGENT FOR REPELLING AND INACTIVATING PATHOGENIC ORGANISMS OF PLANTS

(75) Inventors: Jan Nevermann, Norderstedt (DE); Wolfgang Zerling, Kaltenkirchen (DE); Jutta Hoffler, Hamburg (DE)

(73) Assignee: Menno Chemie Vertriebsges, mbH, Norderstedt (DE)

( * ) Notice: Subject to any disclaimer, the term of this patent is extended or adjusted under 35 U.S.C. 154(b) by 0 days.

(21) Appl. No.: 09/831,216

(22) PCT Filed: Sep. 25, 1999

(86) PCT No.: PCT/EP99/07151

§ 371 (c)(1),
(2), (4) Date: May 4, 2001

(87) PCT Pub. No.: WO00/27192

PCT Pub. Date: May 18, 2000

(30) Foreign Application Priority Data

May 11, 1998 (DE) ................................ 198 50 994

(51) Int. Cl.
- *A01N 37/10* (2006.01)
- *A01N 25/00* (2006.01)
- *A01N 25/32* (2006.01)

(52) U.S. Cl. ................ 514/568; 424/405; 424/406
(58) Field of Classification Search ................ 514/568; 424/405, 406
See application file for complete search history.

(56) References Cited

U.S. PATENT DOCUMENTS

| 4,414,128 A | * | 11/1983 | Goffinet | ................ 510/405 |
| 4,904,683 A | | 2/1990 | Ligtvoet et al. | ............ 514/397 |

FOREIGN PATENT DOCUMENTS

| DE | 3229097 A | | 2/1984 |
| DE | 343885 A | | 3/1986 |
| DE | 4233806 A | | 4/1994 |
| EP | 0091213 A | | 10/1983 |
| WO | WO96 11572 A | | 4/1996 |
| WO | WO-9611572- | * | 4/1996 |

OTHER PUBLICATIONS

Merck Index, 11th ed., 1989, monograph 1101.*
International Search Report in corresponding PCT International application PCT/EP99/07151, listing all the above references, dated Nov. 1, 2000 (6 pages).

* cited by examiner

*Primary Examiner*—San-Ming Hui
(74) *Attorney, Agent, or Firm*—Nashand Titus, LLC

(57) ABSTRACT

The invention relates to disinfecting agents for combating and inactivating phytopathogenic organisms for use on plants and in their environment. The agents are based on a mixture of anionic, active surfactants, aliphatic and aromatic carboxylic acids, glycols, hydrotropic agents and aliphatic, monovalent alcohol, and are characterized in that they contain, together with hydrotropic agents and monovalent alcohols, a combination of aliphatic and aromatic carboxylic acids determined from alkyl- and/or alkylarylsulfonates as well as contain glycols determined individually or in a mixture as solvent.

7 Claims, No Drawings

AGENT FOR REPELLING AND INACTIVATING PATHOGENIC ORGANISMS OF PLANTS

BACKGROUND OF THE INVENTION

Every year, truck farms, meristem operations and plant cultivators sustain great damage due to organisms that infect sets (e.g. plantlets), young plants, mother plants and seeds, destroying them or rendering them useless. If, for example, viruses enter a cultivation, it can be assumed that 100% of the plants will be damaged. The only option open to the truck farms then is the radical measure of destroying the entire culture.

Specifically active agents are commercially available with which a few phytopathogens can be combated without influencing the vitality of the plant. These agents, designated as pesticides, are systemically effective but usually have only a narrow spectrum of activity.

On the other hand, a significantly broader spectrum of activity is offered by common disinfecting agents based on aldehydes, phenols, halogens, peroxides and quaternary ammonium compounds. If these "surface disinfecting agents" get on the plant or are directly applied to the plant, this always entails irreversible damage to the plant. This means that such disinfecting agents can only be used on working surfaces, positioning surfaces and devices such as, e.g., knives and the like. The surfaces must be freed thereafter from adhering remnants of active substances in order not to endanger the plants during subsequent working steps.

However, a sufficient inactivation is not even assured on surfaces since these agents always exhibit significant gaps in their activity against phytopathogenic organisms.

DE OS 32 27 126 and DE OS 32 29 097 teach that certain combinations of anionic surfactants, aliphatic and aromatic carboxylic acids as well as a few heteroaromatic acids are capable of comprehensively killing off or inactivating viruses, bacteria and fungi without gaps in their activity.

The microbes tested according to the above-cited Offenlegungsschriften and patents were primarily human-pathogenic organisms with a low infectiousness like those recommended as test microbes by, among others, the German Society for Hygiene and Microbiology (DGHM) and the German Society for Veterinary Medicine (DVG).

The application of the teaching to highly infectious and resistant phytopathogenic organisms displayed a microbicidal and virus-inactivating activity that was just as persevering as had already been shown to be the case with the human-pathogenic test germs.

However, further tests for plant compatibility with the same agents regularly resulted in a damaging of the test plants in the form of severe scorching, so that the use on plants appeared to be excluded.

It was surprisingly found that the use of certain acid combinations and surfactant combinations in the presence of glycols overcomes the previous deficiency in the combating of phytopathogenic organisms, and that, when applied directly onto a plant, they retain a pronounced bactericidal, fungicidal and viricidal activity and do not damage the plant cells (roots, stems, leaves, flowers and fruit) in the application concentration.

SUMMARY OF THE INVENTION

The present invention relates to agents for treating plants and their environment with the goal of killing off phytopathogenic bacteria, fungi, viruses and viroids and of hindering their spread. Even pathogens (e.g., viruses) that are already on plants can be killed off or inactivated by these agents by moistening roots, stems, leaves and flowers without damaging the plant cells. The biological behavior of the plant is also not altered by the treatment. Working areas in the vicinity of the plants (e.g., tables, knives, positioning surfaces) that could cause a contamination are also freed in a long-lasting manner of noxious organisms therewith without phytotoxic residues having to be subsequently removed.

DETAILED DESCRIPTION OF THE PREFERRED EMBODIMENTS OF THE INVENTION

The invention is further described in the following non-limiting examples.

EXAMPLE 1

| Components | Parts by weight (%) |
| --- | --- |
| Alkylarylsulfonate potassium | 8.50% by wt. |
| Propane diol-1,2 | 20.50 |
| Toluene sulfonate potassium | 10.00 |
| p-Hydroxybenzoic acid | 6.90 |
| Hydroxyethanoic acid | 3.80 |
| Propanol-2 | 28.00 |
| Water (desalinated) | 18.50 |

EXAMPLE 2

| Components | Parts by weight (%) |
| --- | --- |
| Alkylsulfonate potassium | 10.00% by wt. |
| Ethane diol-1,2 | 15.00 |
| Cumene [cumol] sulfonate potassium | 10.00 |
| p-Hydroxybenzoic acid | 6.90 |
| Oxoethanoic acid | 7.00 |
| Propanol-1 | 15.00 |
| Propanol-2 | 15.00 |
| Water (desalinated) | 18.50 |

EXAMPLE 3

| Components | Parts by weight (%) |
| --- | --- |
| Alkylarylsulfonate potassium | 12.00% by wt. |
| Ethane diol-1,2 | 18.00 |
| Cumene [cumol] sulfonate potassium | 8.00 |
| Benzoic acid | 7.00 |
| 2-Hydroxypropionic acid | 7.00 |
| Propanol-1 | 20.00 |
| Propanol-2 | 15.00 |
| Water (desalinated) | 13.00 |

EXAMPLE 4

| Components | Parts by weight (%) |
|---|---|
| Alkylsulfonate (C8–C18) potassium | 7.00% by wt. |
| Alkylsulfonate (C12) potassium | 3.00 |
| Ethane diol-1,2 | 12.00 |
| Cumene [cumol] sulfonate potassium | 11.50 |
| Benzoic acid | 9.00 |
| 2-Hydroxyethanoic acid | 4.50 |
| Propanol-1 | 15.00 |
| Propanol-2 | 15.00 |
| Water (desalinated) | 23.00 |

EXAMPLE 5

| Components | Parts by weight (%) |
|---|---|
| Alkylarylsulfonate sodium | 12.00% by wt. |
| Cumene [cumol] sulfonate sodium | 8.50 |
| o-Hydroxybenzoic acid | 9.50 |
| 2-Hydroxypropionic acid | 5.00 |
| Propanol-1 | 22.00 |
| Propanol-2 | 20.00 |
| Water (desalinated) | 23.50 |

Bactericidal Activity on the Plant (Biotest)

A. Young plant pelargoniums and begonias were contaminated by spraying with *Xanthomonas campestris*. A leaf surface of 1 cm$^2$ had 10$^4$ KBE after the contamination.

A treatment with example 4 in concentrations of 1.0%, 2.0% and 3.0% was conducted, also with a spraying method, one hour after the inoculation.

Specimens were taken one hour after the treatment. The germs of the treated and of the untreated controls (without example 4) were removed from the leaves by ultrasound (wash liquid of 0° C.) and their number determined.

B. Pelargoniums and begonias were treated by spraying with example 4.

The contamination with *Xanthomonas campestris* took place, also with a spraying method, 24 hours after the treatment with example 4.

Specimens were taken one hour after the contamination. The germs of the treated and of the untreated controls (without example 4) were removed from the leaves by ultrasound (wash liquid of 0° C.) and their number determined.

Scorching, lesions on the leaf edges and the leaf blades, germ reduction and leaf compatibility are cited in the following table:

| | Pelargoniums | | Begonias | |
|---|---|---|---|---|
| Concentration | Germ reduction | Toxic phenomena on leaves | Germ reduction | Toxic phenomena on leaves |
| A | | | | |
| 1.0% example 4 | 97%; 93% | No lesions | <99% | No lesions |
| 2.0% example 4 | 100%; 99.5% | No lesions | 99.9% | No lesions |
| 3.0% example 4 | 100%; 99.9% | A few leaf edge lesions | 99.9% | Slight lesions on leaf edges |
| 1.0% example 5 | 98%; 95% | Lesions on the leaf edges | 99.5%; 99.7% | Lesions on the leaf edges and leaf blades |
| 2.0% example 5 | 100%; 100% | Lesions on the leaf edges and leaf blades | 99.9%; 99.9% | Scorching on the leaf edges and the leaf blades |
| 3.0% example 5 | 100%; 94% | Many lesions on the leaf edges and leaf blades | 100%; 100% | Scorching on the leaf edges and the leaf blades |
| B | | | | |
| 1.0% example 4 | 98% | No lesions | 95% | No lesions |

Plant Compatibility

Maximal tolerable concentrations of formulation examples 2, 4 and 5 on plant organs [numerical and sign data require no translation]

| | | Phalaenopsis[1] | Lesions | |
|---|---|---|---|---|
| Examples | Plant organ | Damage | BR | BS |
| 1.0% example 2 | Flowers | 0 | | |
| 2.0% example 2 | | 0 | | |
| 3.0% example 2 | | 0 | | |
| 1.0% example 2 | Leaves | 0 | 0 | 0 |
| 2.0% example 2 | | 0 | 0 | 0 |
| 3.0% example 2 | | + | + | 0 |
| 1.0% example 4 | Flowers | 0 | | |
| 2.0% example 4 | | 0 | | |
| 3.0% example 4 | | 0 | | |
| 1.0% example 4 | Leaves | 0 | 0 | 0 |
| 2.0% example 4 | | 0 | 0 | 0 |
| 3.0% example 4 | | + | ++ | 0 |
| 1.0% example 5 | Flowers | ++ | | |
| 2.0% example 5 | | ++ | | |
| 3.0% example 5 | | +++ | +++ | +++ |
| 1.0% example 5 | Leaves | + | ++ | ++ |
| 2.0% example 5 | | ++ | +++ | ++ |
| 3.0% example 5 | | +++ | +++ | +++ |

Lesion. = Lesions
+++ = very many/very heavily damaged
++ = very/heavily damaged
+ = few/slightly damaged
0 = none/not damaged
BR = leaf edges
BS = leaf blades
[1]orchid type The test for a sufficient inactivation of phytopathogenic organisms gave in the following results:

1. Bactericidal action of examples 1–5 in a lab test according to "Guideline 16-4 for the Testing of Plant Protection Products for Disinfection in the Cultivation of Decorative Plants" of the Biological Federal Institute for Agriculture and Forestry (Braunschweig, 1986)

Required Contact Times of Examples 1–5 for Killing Off the Indicated Bacterial Strains 2. Fungicidal action of examples 1–5 in a lab test according to "Guideline 16-4 for the Testing of Plant Protection Products for Disinfection in the Cultivation of Decorative Plants" of the Biological Federal Institute for Agriculture and Forestry (Braunschweig, 1986)

Required Contact Times of Examples 1–5 for Killing Off the Indicated Fungus Test Strains

| Example | Fusarium oxysporum | Thielaviopsis basicola | Phythophtora sp | Cylindrocladium scoparium |
|---|---|---|---|---|
| Tap water control | No activity | No activity | No activity | No activity |
| 1.0% example 1 | 16 h | >16 h | 1 h | >16 h |
| 2.0% example 1 | 4 h | 4 h | 1 h | >16 h |
| 1.0% example 2 | 4 h | 4 h | 1 h | >16 h |
| 2.0% example 2 | 1 h | 1 h | 5 min | 16 h |
| 1.0% example 3 | 4 h | 16 h | 1 h | 16 h |
| 2.0% example 3 | 4 h | 4 h | 30 min | 4 h |
| 1.0% example 4 | 1 h | 4 h | 30 min | 16 h |
| 2.0% example 4 | 1 h | 1 h | 15 min | 4 h |
| 1.0% example 5 | 1 h | 4 h | 1 h | 16 h |
| 2.0% example 5 | 1 h | 1 h | 5 min | 16 h |

Required Contact Times of Examples 1–5 for Inactivating the Indicated Viral Strains (Suspension Test)

| Disinfecting agent | TMV | PBY | PFBV | CNV | ORSV | PSTVd |
|---|---|---|---|---|---|---|
| Tap water control | No activity | No activity | No activity | No activity | No activity | No activity |
| 1.0% example 1 | 16 h | 16 h | 4 h | 16 h | 4 h | 4 h |
| 2.0% example 1 | 16 h | 4 h | 1 h | 4 h | 1 h | 1 h |
| 3.0% example 1 | 16 h | 4 h | 1 h | 4 h | 1 h | <1 h |
| 1.0% example 2 | >16 h | 16 h | 4 h | 16 h | 1 h | 4 h |
| 2.0% example 2 | 16 h | 4 h | 1 h | 4 h | <1 h | 1 h |
| 3.0% example 2 | 4 h | 4 h | 1 h | 4 h | <1 h | 1 h |
| 1.0% example 3 | >16 h | 16 h | 4 h | 1 h | 4 h | 4 h |
| 2.0% example 3 | 16 h | 4 h | 1 h | <1 h | 4 h | 1 h |
| 3.0% example 3 | 16 h | 4 h | 1 h | <1 h | 1 h | 1 h |
| 1.0% example 4 | 4 h | 4 h | 1 h | <1 h | 4 h | 1 h |
| 2.0% example 4 | 4 h | 1 h | <1 h | <1 h | 1 h | <1 h |
| 3.0% example 4 | 1 h | 1 h | <1 h | <1 h | 1 h | <1 h |
| 1.0% example 5 | 4 h | 4 h | 1 h | <1 h | 4 h | 1 h |
| 2.0% example 5 | 4 h | 4 h | 1 h | <1 h | 1 h | 1 h |
| 3.0% example 5 | 1 h | 1 h | <1 h | <1 h | 1 h | <1 h |

TMV = Tobacco mosaic virus
PVY = Potato virus Y Potyvirus
PFBV = Pelargonium flower break carmovirus
CNV = Cucumber necrosis tombuvirus
ORSV = Odontoglossum ringspot virus
PSTVd = Potato spindle tuber viroid The test for a sufficient inactivation of phytopathogenic organisms gave in the following results:

1. Bactericidal action of examples 1–5 in a lab test according to "Guideline 16-4 for the Testing of Plant Protection Products for Disinfection in the Cultivation of Decorative Plants" of the Biological Federal Institute for Agriculture and Forestry (Braunschweig, 1986)

Required Contact Times of Examples 1–5 for Killing Off the Indicated Bacterial Strains

| Examples | Xanthomonas pelargonii | Pseudomonas solanaceum | Erwinia amylovora |
|---|---|---|---|
| Tap water control | No activity | No activity | No activity |
| 1.0% example 1 | 1 min. | 1 min. | 5 min. |
| 1.0% example 2 | 1 min. | 1 min | 1 min |
| 1.0% example 3 | 5 min | 5 min | 15 min |
| 1.0% example 4 | 1 min | 1 min | 1 min |
| 1.0% example 5 | 1 min | 1 min | 1 min |

The invention claimed is:

1. A disinfecting agent for combating and inactivating phytopathogenic organisms that are present on plants and on hard surfaces surrounding the plants, said agent comprising at least one anionic surfactant, at least one aliphatic carboxylic acid, at least one aromatic carboxylic acid, mono-, di- and/or triglycols, at least one hydrotropic agent and at least one primary and/or secondary aliphatic, monovalent alcohol having a chain length of $C_2$ to $C_8$ in aqueous solution, wherein said agent, when contacted with phytopathogenic organisms present on plants or on hard surfaces, kills or inactivates the phytopathogenic organisms without damaging the plants and without leaving phytotoxic residues on the hard surfaces, wherein the aliphatic and aromatic carboxylic acids are selected from the group consisting of methanoic acid, ethanoic acid, propanoic acid, hydroxyethanoic acid, 2-hydroxypropionic acid, oxoethanoic acid, 2-oxopropionic acid, 4-oxovaleric acid, benzoic acid, o-, m-, p-hydroxybenzoic acids, 3,4,5-tri-hydroxybenzoic acid, and mixtures thereof, and wherein the anionic surfactant has a primary chains of a length of $C_8$–$C_{18}$ and is selected from the group consisting of alkyl sulfonates, alkylarylsulfonates, the sodium-, potassium- and ammonium salts of alkyl sulfonates and alkylarylsulfonates, wherein the mono-, di- and/or triglycols are selected from the group consisting of ethylene glycol, propylene glycol, 2,3-butylene glycol, diethylene glycol [2,2'-dihydroxydiethylether], triethylene glycol [(1,2-di-2-hydroxyethoxyl-ethane], and mixtures thereof, and wherein the hydrotropic agent is selected from the group consisting of toluene sulfonate and cumene sulfonate as sodium- or potassium salts.

2. The disinfecting agent according to claim 1, wherein the weight ratio of the aliphatic acids (A) to the aromatic acids (B) is between 1:9 and 9:1 and their sum is between 5 and 40% by wt. relative to the total weight of the disinfecting-agent concentrate.

3. The disinfecting agent according to claim 2, wherein the weight ratio of the alkyl sulfonates and/or alkylarylsulfates and their salts (C) with the acids (A+B) in the ratio C:(B+A) is between 1:9 and 9:1 and their sum is between 10 and 60% relative to the total weight of the disinfecting-agent concentrate.

4. The disinfecting agent according to claim 1, wherein the weight component of the glycols relative to the total weight of the disinfecting-agent concentrate is between 10 and 40% by wt.

5. The disinfecting agent according to claim 1, wherein the weight ratio of the hydrotropic agents toluene sulfonate and cumene sulfonate, their sodium- or potassium salts, individually or in a mixture with each other, is between 5 and 40% by wt. relative to the total weight of the disinfecting-agent concentrate.

6. The disinfecting agent according to claim 1, wherein the weight ratio of the monovalent alcohols, individually or in a mixture with each other, is between 5 and 60% by wt. relative to the total weight of the disinfecting-agent concentrate.

7. A method for combating phytopathogenic microorganisms present on a plant or on hard surfaces surrounding the plant, comprising the step of applying to the plant and/or to its immediate environment a composition containing 0.5 to 10% by wt. of a disinfection agent concentrate in dilute aqueous solution, which disinfecting agent comprises at least one anionic surfactant, at least one aliphatic carboxylic acid, at least one aromatic carboxylic acid, mono-, di- and/or triglycols, at least one hydrotropic agent and at least one primary and/or secondary aliphatic, monovalent alcohol having a chain length of $C_2$ to $C_8$ in aqueous solution, wherein said agent, when contacted with phytopathogenic organisms present on plants or on hard surfaces, kills or inactivates the phytopathogenic organisms without damaging the plants and without leaving phytotoxic residues on the hard surfaces, wherein the aliphatic and aromatic carboxylic acids are selected from the group consisting of methanoic acid, ethanoic acid, propanoic acid, hydroxyethanoic acid, 2-hydroxypropionic acid, oxoethanoic acid, 2-oxopropionic acid, 4-oxovaleric acid, benzoic acid, o-, m-, p-hydroxybenzoic acids, 3,4,5-tri-hydroxybenzoic acid, and mixtures thereof, and wherein the anionic surfactant has a primary chains of a length of $C_8$–$C_{18}$ and is selected from the group consisting of alkyl sulfonates, alkylarylsulfonates, the sodium-, potassium- and ammonium salts of alkyl sulfonates and alkylarylsulfonates, wherein the mono-, di- and/or triglycols are selected from the group consisting of ethylene glycol, propylene glycol, 2,3-butylene glycol, diethylene glycol [2,2'-dihydroxydiethylether], triethylene glycol [(1,2-di-2-hydroxyethoxyl-ethane], and mixtures thereof, and wherein the hydrotropic agent is selected from the group consisting of toluene sulfonate and cumene sulfonate as sodium- or potassium salts.

\* \* \* \* \*